(12) United States Patent
Yang et al.

(10) Patent No.: US 10,160,980 B2
(45) Date of Patent: Dec. 25, 2018

(54) ARTIFICIAL PHOTOSYNTHESIS SYSTEMS AND METHODS FOR PRODUCING CARBON-BASED CHEMICAL COMPOUNDS

(71) Applicant: The Regents of the University of California, Oakland, CA (US)

(72) Inventors: Peidong Yang, Kensington, CA (US); Michelle C. Y. Chang, Berkeley, CA (US); Christopher J. Chang, Berkeley, CA (US); Chong Liu, Cambridge, MA (US); Joseph J. Gallagher, Berkeley, CA (US); Eva M. Nichols, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 211 days.

(21) Appl. No.: 15/061,378

(22) Filed: Mar. 4, 2016

(65) Prior Publication Data
US 2016/0264920 A1 Sep. 15, 2016

Related U.S. Application Data

(60) Provisional application No. 62/131,627, filed on Mar. 11, 2015, provisional application No. 62/250,878, filed on Nov. 4, 2015.

(51) Int. Cl.
| | |
|---|---|
| *C12M 1/00* | (2006.01) |
| *C12P 5/02* | (2006.01) |
| *C12P 7/54* | (2006.01) |
| *C25B 1/00* | (2006.01) |
| *C25B 1/10* | (2006.01) |
| *C25B 9/08* | (2006.01) |
| *C25B 11/02* | (2006.01) |
| *C25B 11/04* | (2006.01) |

(52) U.S. Cl.
CPC ............ *C12P 5/023* (2013.01); *C12M 23/34* (2013.01); *C12M 29/04* (2013.01); *C12M 43/00* (2013.01); *C12M 43/06* (2013.01); *C12P 7/54* (2013.01); *C25B 1/003* (2013.01); *C25B 1/10* (2013.01); *C25B 9/08* (2013.01); *C25B 11/02* (2013.01); *C25B 11/04* (2013.01); *Y02E 50/343* (2013.01)

(58) Field of Classification Search
None
See application file for complete search history.

(56) References Cited

PUBLICATIONS

Anbarasan P, et al. Integration of chemical catalysis with extractive fermentation to produce fuels. Nature, 2012, 491(7423):235-239.
Appel AM et al. Frontiers, Opportunities, and Challenges in Biochemical and Chemical Catalysis of CO2 Fixation. Chem Rev, 2013, 113(8):6621-6658.
Blankenship RE, et al. Comparing Photosynthetic and Photovoltaic Efficiencies and Recognizing the Potential for Improvement. Science, 2011, 332(6031):805-809.
Brillet J, et al. Highly efficient water splitting by a dual-absorber tandem cell. Nat Photonics, 2012, 6:824-828.
Cheng S, et al. Direct biological conversion of electrical current into methane by electromethanogenesis. Environ Sci Technol, 2009, 43(10):3953-3958.
Cox CR, et al. Ten-percent solar-to-fuel conversion with nonprecious materials. Proc Natl Acad Sci USA, 2014, 111 (39):14057-14061.
Daniels L, et al. Bacterial methanogenesis and growth from CO2 with elemental iron as the sole source of electrons. Science, 1987, 237(4814):509-511.
Lovely DR and Nevin KR Electrobiocommodities: Powering microbial production of fuels and commodity chemicals from carbon dioxide with electricity. Curr Opin Biotechnol, 2013, 24(3):385-390.
Gray HB. Powering the planet with solar fuel. Nat Chem, 2009, 1(1):7.
Jhong H, et al. Electrochemical conversion of CO2 to useful chemicals: Current status, remaining challenges, and future opportunities. Curr Opin Chem Eng, 2013, 2(2):191-199.
Keasling JD. Manufacturing Molecules Through Metabolic Engineering. Science, 2010, 330(6009):1355-1358.
Khaselev OA and Turner JA. A monolithic photovoltaic-photoelectrochemical device for hydrogen production via water splitting. Science, 1998, 280(5362):425-427.
Lewis NA and Nocera DG. Powering the planet: Chemical challenges in solar energy utilization. Proc Natl Acad Sci USA, 2006, 103(43):15729-15735.
Li H, et al. Integrated electromicrobial conversion of CO2 to higher alcohols. Science, 2012, 335(6076):1596.
Liu B and Aydil ES. Growth of oriented single-crystalline rutile TiO2 nanorods on transparent conducting substrates or dye-sensitized solar cells. J Am Chem Soc, 2009, 131(11):3985-3990.
Liu C et al. A fully integrated nanosystem of semiconductor nanowires for direct solar water splitting. Nano Lett, 2013, 13(6):2989-2992.

(Continued)

*Primary Examiner* — Anand U Desai

(57) ABSTRACT

This disclosure provides systems, methods, and apparatus related to artificial photosynthesis. In one aspect a system includes a photoanode chamber including a photoanode assembly, a photocathode chamber including a photocathode assembly, an electrical connection electrically connecting the photoanode assembly and the photocathode assembly, a membrane separating the photoanode chamber and the photocathode chamber, and a microorganism disposed in the photocathode chamber. The photoanode assembly is operable to oxidize water to generate oxygen, protons, and electrons. The membrane is permeable to the protons and operable to allow the protons to travel to the photocathode chamber. The electrical connection provides electrons to the photocathode assembly. The microorganism comprises a metabolic pathway to reduce carbon dioxide and to generate a carbon-based compound using the electrons or hydrogen formed by two protons.

20 Claims, 7 Drawing Sheets

(56) References Cited

PUBLICATIONS

Nichols, Eva M, et al. Hybrid bioinorganic approach to solar—to chemical conversion. PNAS, Sep. 15, 2015, vol. 112, No. 37, pp. 11461-11466.

Liu C, et al. Semiconductor Nanowires for Artificial Photosynthesis. P. Chem. Mater., 2013, 26(1):415-422.

Luo J, et al. Water photolysis at 12.3% efficiency via perovskite photovoltaics and Earth-abundant catalysts. Science, 2014, 345(6204):1593-1596.

Lyon EJ, et al. UV-A/blue-light inactivation of the "metal-free" hydrogenase (Hmd) from methanogenic archaea. Eur J Biochem, 2004, 271(1):195-204.

Mah RA, et al. Studies on an acetate-fermenting strain of Methanosarcina. Appl Environ Microbial, 1978, 35(6):1174-1184.

Meyer, TJ. Chemical approached to artificial photosynthesis. Acc Chem Res, 1989, 22(5):163-170.

Moller B, et al. *Sporomusa*, a new genus of gram-negative anaerobic bacteria including *Sporomusa sphaeroides* spec. nov. and *Sporomusa ovata* spec. nov. Arch Microbial., 1984, 139:388-396.

Nevin KP et al. Microbial electrosynthesis: Feeding microbes electricity to convert carbon dioxide and water to multicarbon extracellular organic compounds. MBio, 2010, 1(2):e00103-e00110.

Nozik AJ. p-n. photaelectralysis cells. J. Appl. Phys. Lett, 1976, 29, 150.

Olson KD, et al. Light sensitivity of methanogenic archaebacteria. Appl Environ Microbiol, 1991, 57(9):2683-2686.

Parkin A et al. Rapid and efficient electrocatalytic CO2/CO interconversions by Carboxydothermus hydrogenoformans CO dehydrogenase I on an electrode. J Am Chem Soc, 2007, 129(34):10328-10329.

Parkinson BA and Weaver PF Photoelectrochemical pumping of enzymatic CO2 reduction. Nature, 1984, 309 (5964):148-149.

Rabaey K and Rozendal RA. Microbial electrosynthesis—revisiting the electrical route for microbial production. Nat Rev Microbiol, 2010, 8(10):706-716.

Reda T et al. Reversible interconversion of carbon dioxide and formate by an electroactive enzyme. Proc Natl Acad Sci USA, 2008, 105(31):10654-10658.

Reece SY, et al. Wireless Solar Water Splitting Using Silicon-Based Semiconductors and Earth-Abundant Catalysts. Science, 2011, 334(6056):645-648.

Schlegel HG and Lafferty R. Growth of "Knallgas" bacteria (*Hydrogenomonas*) using direct electrolysis of the culture medium. Nature, 1965, 205(4968):308-309.

Shin W et al. Highly Selective Electrocatalytic Conversion of CO2 to CO at -0.57 V (NHE) by Carbon Monoxide Dehydrogenase from Moorella thermoacetica. J Am Chem Soc, 2003, 125(48):14688-14689.

Siegert M, et al. Comparison of nonprecious metal cathode materials for methane production by electromethanogenesis. ACS Sustain Chem Eng, 2014, 2(4):910-917.

Sirasani G, et al. A biocompatible alkene hydrogenation merges organic synthesis with microbial metabolism. Angew Chem Int Ed Engl, 2014, 53(30):7785-7788.

Song J, et al. Microbes as electrochemical CO2 conversion catalysts. Chem Sus Chem, 2011, 4(5):587-590.

Thauer RK. Biochemistry of methanogenesis: A tribute to Marjory Stephenson. 1998 Marjory Stephenson Prize Lecture. Microbiology, 1998, 144(Pt 9):2377-2406.

Torella JP, et al. Efficient solar-to-fuels production from a hybrid microbial-water-splitting catalyst system. Proc Natl Acad Sci USA, 2015, 112(8):2337-2342.

Van Eerten-Jansen MC, et al. Microbial community analysis of a methane-producing biocathode in a bioelectrochemical system. Archaea, 2013, 2013:481784.

Villano M, et al. Bioelectrochemical reduction of CO2 to CH4 via direct and indirect extracellular electron transfer by a hydrogenophilic methanogenic culture. Bioresour Technol, 2010, 101(9):3085-3090.

Woolerton TW et al. Efficient and clean photoreduction of CO2 to CO by enzyme-modified TiO2 nanoparticles using visible light. J Am Chem Soc, 2010, 132(7):2132-2133.

Zeng K and Zhang D. Recent progress in alkaline water electrolysis for hydrogen production and applications. Prog Energy Combust Sci, 2010, 36(3):307-326.

Liu, Chong, et al. Nanowire—Bacteria Hybrids for Unassisted Solar Carbon Dioxide Fixation to Value-Added Chemicals. Nano Lett., 2015, 15 (5), pp. 3634-3639.

ARTIFICIAL PHOTOSYNTHESIS SYSTEMS AND METHODS FOR PRODUCING CARBON-BASED CHEMICAL COMPOUNDS

RELATED APPLICATIONS

This application claims priority to U.S. Provisional Patent Application No. 62/131,627, filed Mar. 11, 2015 and to U.S. Provisional Patent Application No. 62/250,878, filed Nov. 4, 2015, both of which are hereby incorporated by reference.

STATEMENT OF GOVERNMENT SUPPORT

This invention was made with government support under Contract No. DE-AC02-05CH11231 awarded by the U.S. Department of Energy. The government has certain rights in this invention.

TECHNICAL FIELD

This disclosure relates generally to artificial photosynthesis and more particularly to systems for and methods of artificial photosynthesis.

BACKGROUND

Methods for the sustainable conversion of carbon dioxide to value-added chemical products are of technological and societal importance. Elegant advances in traditional approaches to $CO_2$ reduction driven by electrical and/or solar inputs using homogeneous, heterogeneous, and biological catalysts point out key challenges in this area, namely: (i) the chemoselective conversion of $CO_2$ to a single product while minimizing the competitive reduction of protons to hydrogen; (ii) long-term stability under environmentally friendly aqueous conditions; and (iii) unassisted light-driven $CO_2$ reduction that does not require external electrical bias and/or sacrificial chemical quenchers. Synthetic homogeneous and heterogeneous $CO_2$ catalysts are often limited by product selectivity and/or aqueous compatibility, whereas enzymes show specificity but are generally less robust outside of their protective cellular environment. In addition, the conversion of electrosynthetic systems to photosynthetic ones is nontrivial owing to the complexities of effectively integrating components of light capture with bond-making and bond-breaking chemistry.

SUMMARY

Inspired by the process of natural photosynthesis in which light-harvesting, charge-transfer, and catalytic functions are integrated to achieve solar-driven $CO_2$ fixation, a program in solar-to-chemical conversion to harness the strengths inherent to both inorganic materials chemistry and biology was started. As shown in FIG. 1A, one strategy to drive synthesis with sustainable electrical and/or solar energy input interfaces a biocompatible photo(electro)chemical hydrogen evolution reaction (HER) catalyst with a microorganism that uses this sustainably generated hydrogen as an electron donor for $CO_2$ reduction.

In comparison with fully inorganic catalysts, a distinct conceptual advantage of this hybrid materials biology approach, where the materials component performs water splitting to generate hydrogen and the biological component uses these reducing equivalents for $CO_2$ fixation, is that one can leverage the fact that biological catalysts operate at near thermodynamic potential. As such, the only overpotential involved is associated with hydrogen evolution from water, a more facile reaction to catalyze via sustainable electrochemical and photochemical means compared with $CO_2$ reduction.

When in operation, the systems described herein mimic natural photosynthesis. Light capture by biocompatible nanowires can interface and directly provide reducing equivalents (e.g., electrons or hydrogen) to living organisms for the targeted synthesis of value-added chemical products from $CO_2$ fixation. Such an integration between materials science and biology separates the demanding dual requirements for light-capture efficiency and catalytic activity, respectively, and provides a route to bridge efficient solar conversion in robust solid-state devices with the broad synthetic capabilities of living cells.

One innovative aspect of the subject matter described in this disclosure can be implemented in an apparatus including a photoanode chamber including a photoanode assembly, a photocathode chamber including a photocathode assembly, an electrical connection electrically connecting the photoanode assembly and the photocathode assembly, a membrane separating the photoanode chamber and the photocathode chamber, and a microorganism disposed in the photocathode chamber. The photoanode assembly comprises a first plurality of nanostructures disposed on a first substrate. The photocathode assembly comprises a second plurality of nanostructures disposed on a second substrate. The photoanode assembly is operable to oxidize water to generate oxygen, protons, and electrons. The membrane is permeable to the protons and operable to allow the protons to travel to the photocathode chamber. The electrical connection is operable to provide electrons to the photocathode assembly. The microorganism comprises a metabolic pathway to reduce carbon dioxide and to generate a carbon-based compound using the electrons or hydrogen formed by two protons.

In some implementations, the first plurality of nanostructures comprises titanium oxide, the second plurality of nanostructures comprises silicon, the microorganism comprises *Sporomsa ovata*, and the carbon-based compound comprises acetate. In some implementations, the first plurality of nano structures comprises titanium oxide, the second plurality of nanostructures comprises indium phosphide, the microorganism comprises *Methansarcina barkeri*, and the carbon-based compound comprises methane.

Another innovative aspect of the subject matter described in this disclosure can be implemented in a method including providing a device comprising a photoanode chamber including a photoanode assembly, a photocathode chamber including a photocathode assembly, an electrical connection electrically connecting the photoanode assembly and the photocathode assembly, a membrane separating the photoanode chamber and the photocathode chamber, and a microorganism disposed in the photocathode chamber. The photoanode assembly comprises a first plurality of nanostructures disposed on a first substrate. The photocathode assembly comprises a second plurality of nanostructures disposed on a second substrate. The photoanode, the photocathode, and the membrane are disposed in water. The membrane is impermeable to oxygen and oxygen radicals. The photoanode assembly is irradiated with a first light and the photocathode assembly is irradiated with a second light. The photoanode oxidizes the water to generate oxygen, protons, and electrons. The electrons are provided to the photocathode assembly by the electrical connection. The protons travel through the membrane to the photocathode chamber. A carbon-based compound is formed by the microorganism using the electrons or hydrogen formed by two protons.

In some implementations, the water has about 0.5 grams/liter to 30 grams/liter of salt dissolved in the water. In some implementations, the first light includes more wavelengths of light than the second light.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

Figure 1A:
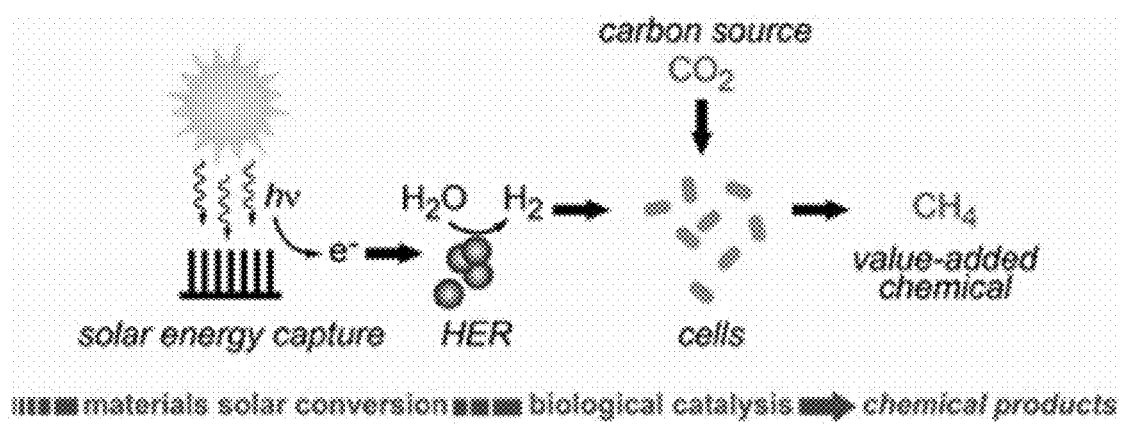
FIG. 1A shows an example of a general scheme of a hybrid bioinorganic approach to solar-to-chemical conversion.
Figure 1B:
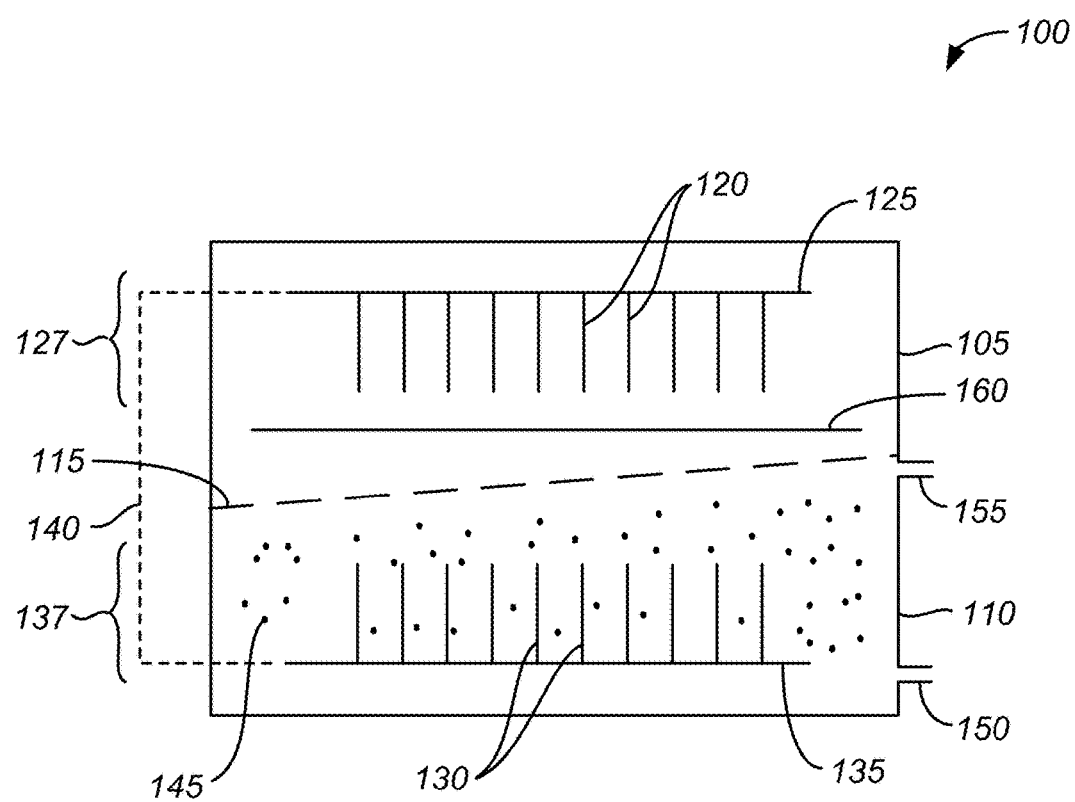
FIG. 1B shows an example of a cross-sectional schematic illustration of an artificial photosynthesis system.
Figure 1C:
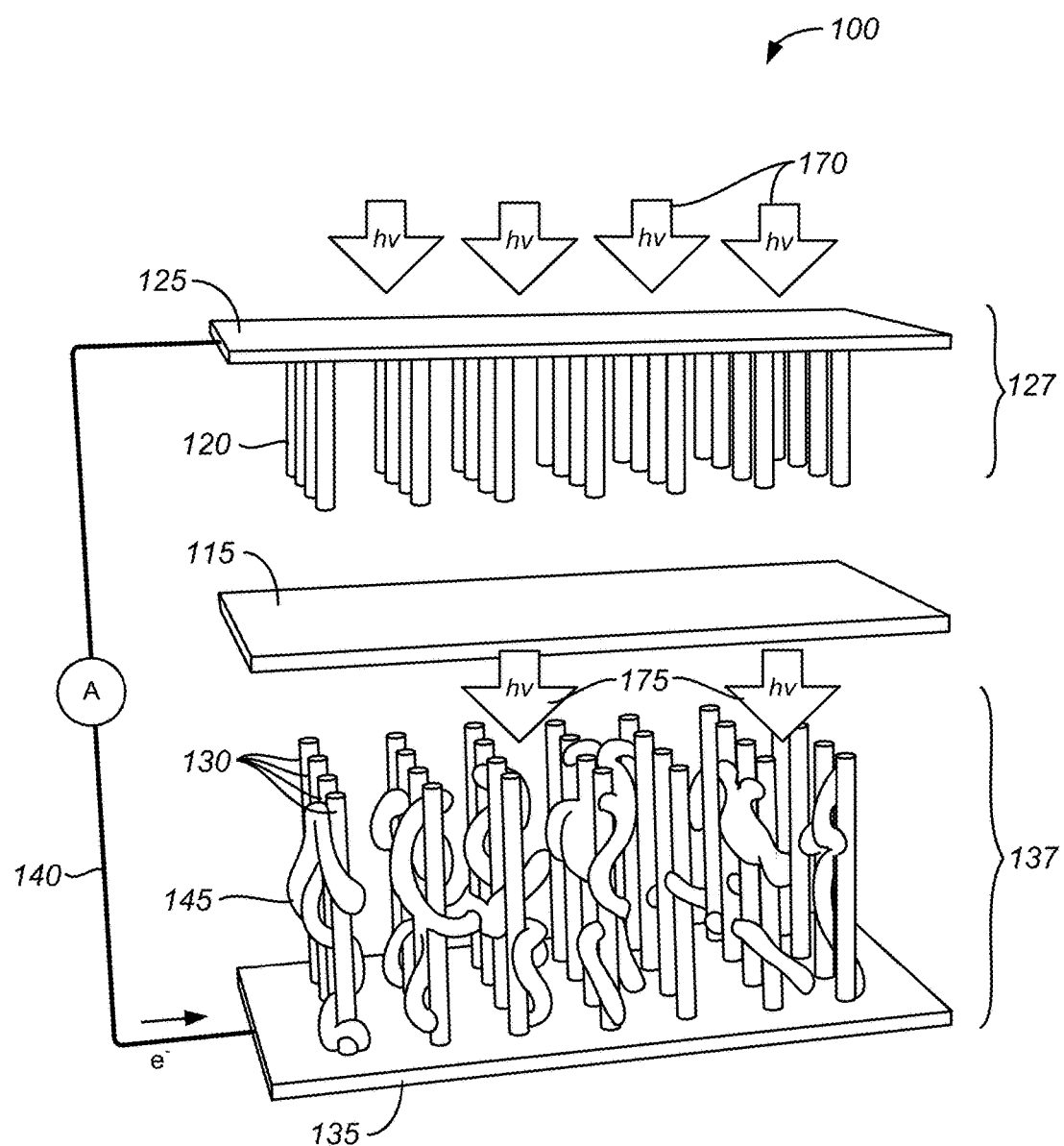
FIG. 1C shows an example of an isometric illustration of an artificial photosynthesis system.

FIG. 1B shows an example of a cross-sectional schematic illustration of an artificial photosynthesis system. FIG. 1C shows an example of an isometric illustration of an artificial photosynthesis system. An artificial photosynthesis system 100 shown FIG. 1B includes a photoanode chamber 105, a photocathode chamber 110, and a membrane 115 separating the photoanode chamber 105 and the photocathode chamber 110; FIG. 1C also shows the artificial photosynthesis system 100, but does not show the photoanode chamber 105 and the photocathode chamber 110. The photoanode chamber 105 includes a photoanode assembly 127. In some embodiments, the photoanode assembly 127 comprises a substrate 125. In some embodiments, the photoanode assembly 127 comprises a plurality of nanowires 120 disposed on the substrate 125. Similarly, the photocathode chamber 110 includes a photocathode assembly 137. In some embodiments, the photocathode assembly 137 comprises a substrate 135. In some embodiments, the photocathode assembly 137 comprises a plurality of nanowires 130 disposed on the substrate 135. An electrical connection 140 electrically connects the photoanode assembly 127 and the photocathode assembly 137. A microorganism 145 is disposed in the photocathode chamber 110.

When the system 100 is in operation, the photoanode assembly 127 is operable to oxidize water to generate oxygen, protons, and electrons; $2H_2O \rightarrow O_2 + 4H^+ + 4e^-$. An $H^+$ ion is a proton. In some embodiments, the membrane 115 is permeable to cations. In some embodiments, the membrane 115 is permeable to anions. In some embodiments, the membrane 115 is permeable to the protons and operable to allow the protons to travel to the photocathode chamber 110. Electrons generated by oxidizing water are provided to the photocathode assembly 137 via the electrical connection 140. The electrons in the photocathode assembly provide a driving force for the protons to travel across the membrane 115 to the photocathode chamber 110. The microorganism 145 in the photocathode chamber 110 comprises a metabolic pathway to reduce carbon dioxide and to form a carbon-based compound using the electrons or hydrogen formed by two protons.

For example, in some embodiments, the microorganism 145 receives electrons. The electrons provide the microorganism 145 with energy that is used to reduce carbon dioxide and to form a carbon-based compound. In these embodiments, no hydrogen gas ($H_2$) is formed. In some embodiments, hydrogen gas is formed at the photocathode assembly 137; $2H^+ + 2e^- \rightarrow H_2$. The microorganism 145 uses the hydrogen gas to reduce carbon dioxide and to form a carbon-based compound.

In some embodiments, the photoanode chamber 105 and the photocathode chamber 110 are chambers that are able to hold water or other aqueous solution. For example, in some embodiments, the photoanode chamber 105 and the photocathode chamber 110 comprise a glass. In some embodiments, the photoanode chamber 105 and the photocathode chamber 110 comprise a metal, ceramic, or a plastic. In these embodiments, there are openings or windows in the photoanode chamber 105 and/or the photocathode chamber 110 that allow light to irradiate the photoanode assembly 127 and the photocathode assembly 137. The photoanode chamber 105 and the photocathode chamber 110 together may be considered to be one large chamber, with the membrane 115 separating the chamber into the photoanode chamber 105 and the photocathode chamber 110.

In some embodiments, the substrate 125 or the plurality of nanowires 120 disposed on the substrate 125 of the photoanode assembly 127 comprise an n-type semiconductor. In some embodiments, the nanowires 120 increase the system efficiency compared to having only a substrate 125. In some embodiments, the substrate 125 or plurality of nanowires 120 comprise titanium oxide, tungsten oxide, gallium nitride, gallium arsenide, gallium phosphide, tantalum oxynitride, indium gallium nitride, other oxides, other nitrides, or other oxynitrides. These semiconductor materials may be doped to make them n-type. In some embodiments, each of the plurality of nanowires 120 is about 1 micron to 10 microns long, about 1 micron to 5 microns long, or about 2 microns long. In some embodiments, each of the plurality of nanowires 120 has a cross-sectional dimension (e.g., a diameter) of about 5 nanometers (nm) to 1 micron or about 5 nm to 500 nm. In some embodiments, the substrate 125 is a conductive material. In some embodiments, the substrate 125 comprises a material that allows visible light be transmitted through it. For example, in some embodiments, the substrate 125 comprises the same material as the plurality of nanowires 120 or a metal. In these embodiments, the substrate 125 is thin to allow visible light to be transmitted. In some embodiments, the substrate 125 comprises a glass with indium tin oxide (ITO) or fluorine-doped indium tin oxide disposed thereon.

In some embodiments, the substrate 135 or the plurality of nanowires 130 disposed on the substrate 135 of the photocathode assembly 137 comprise a p-type semiconductor. In some embodiments, the nanowires 130 increase the system efficiency compared to having only a substrate 135. In some embodiments, the nanowires 130 increase the area available for the microorganism to contact the photocathode assembly 137. In some embodiments, the substrate 135 or the plurality of nanowires 130 comprise silicon, germanium, gallium arsenide, gallium phosphide, indium phosphide, or other III-V semiconductor. These semiconductor materials may be doped to make them p-type. In some embodiments, each of the plurality of nanowires 130 is about 15 microns to 45 microns long, or about 30 microns long. In some embodiments, each of the plurality of nanowires 130 has a cross-sectional dimension (e.g., a diameter) of about 5 nm to 1 micron or about 5 nm to 500 nm. In some embodiments, the substrate 135 is a conductive material. In some embodiments, the substrate 135 comprises the same material as the plurality of nanowires 130, a metal, or a semiconductor.

In some embodiments, the substrate 135 or the nanowires of the plurality of nanowires 130 of the photocathode assembly 137 are coated with an oxide layer to passivate the nanowires. Passivating the substrate 135 or the plurality of nanowires 130 may protect them from the aqueous environment that they will be in when the system 100 is in operation. In some embodiments, the oxide of the oxide layer comprises titanium oxide ($TiO_2$), silicon dioxide ($SiO_2$), tin oxide ($SnO_2$), indium tin oxide (ITO), of fluorine-doped tin oxide (FTO). In some embodiments, the oxide layer has a thickness of about 15 nm to 45 nm, or about 30 nm.

In some embodiments, the substrate 135 or the nanowires of the plurality of nanowires 130 of the photocathode assembly 137 are coated with a metal layer or a layer of a metallic compound. The metal layer or the layer of a metallic compound may aid in charge transfer from the substrate 135 or the nanowires (i.e., transfer of the electrons) to the microorganism or act as a catalyst for a hydrogen evolution reaction (i.e., $2H^+ + 2e^- \rightarrow H_2$). In some embodiments, the metal layer is about 5 nm to 15 nm thick, about 5 nm thick, or about 10 nm thick. In some embodiments, the metal or metallic compound comprises nickel, cobalt, platinum, a nickel-molybdenum alloy, a nickel phosphorous alloy, a cobalt phosphorous alloy, nickel sulfide/selenide, cobalt sulfide/selenide, molybdenum sulfide/selenide, and nickel/cobalt/iron phosphide. Examples of metals that may be used to aid in charge transfer from the nanowires to the microorganism are nickel and a mixture of nickel and platinum. An example of a metal that may be used as a catalyst for a hydrogen evolution reaction is platinum. In some embodiments, the metal layer is disposed on an oxide layer that serves to passivate the substrate 135 or the nanowires.

Figure 2:
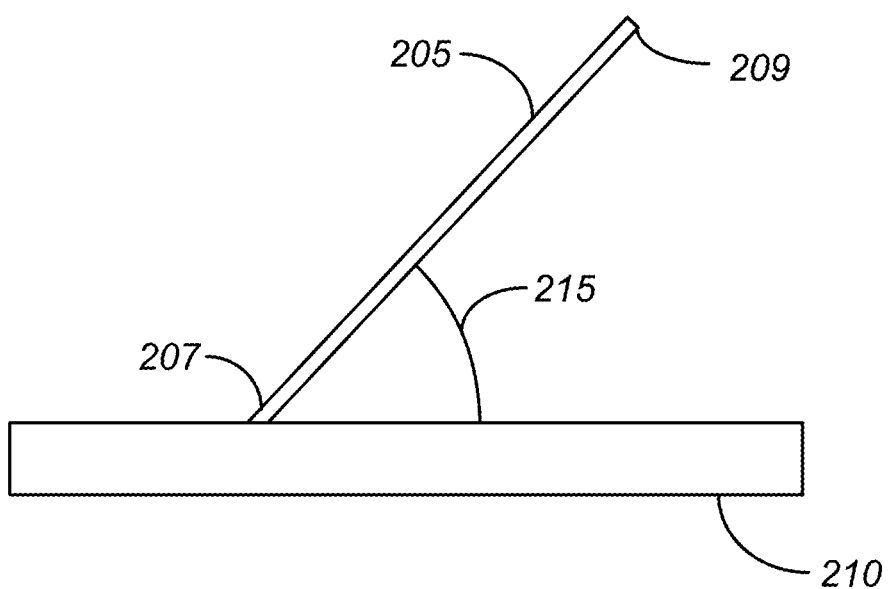
FIG. 2 shows an example of a nanowire disposed on a substrate.

As shown in FIG. 2, in some embodiments, a nanowire 205 forms an angle 215 of about 45° to 90° with a surface of a substrate 210. In some embodiments, an end 207 of the nanowire 205 is in contact with the substrate 210 and an end 209 of the nanowire 205 is not in contract with the substrate 210. Both the plurality of nanowires 120 disposed on the substrate 125 of the photoanode assembly 127 and the plurality of nanowires 130 disposed on the substrate 135 of the photocathode assembly 137 may have a configuration as shown in FIG. 2. In some embodiments, nanowires of the plurality of nanowires disposed on a substrate are substantially parallel to one another.

Returning to FIGS. 1B and 1C, in some embodiments, the electrical connection 140 electrically connecting the photoanode assembly 127 to the photocathode assembly 137 comprises a wire. Other electrical connections may also be used.

In some embodiments, the membrane 115 separating the photoanode chamber 105 and the photocathode chamber 110 is permeable to cations. In some embodiments, the membrane 115 is permeable to protons and is a proton conductor. In some embodiments, the membrane 115 comprises a sulfonated tetrafluoroethylene based fluoropolymer-copolymer. An example of a sulfonated tetrafluoroethylene based fluoropolymer-copolymer is Nafion (Dupont, Wilmington, Del. or Membranes International, Inc., Ringwood, N.J.). Nafion is a permeable to cations or protons. In some embodiments, the membrane 115 is impermeable to gasses. In some embodiments, the membrane 115 is impermeable to oxygen. In some embodiments, the membrane 115 is impermeable to oxygen and oxygen radicals. In some embodiments, the microorganism 145 is an anaerobic microorganism, and oxygen may kill the microorganism. For example, about 50 ppm or greater oxygen dissolved in the water may kill the microorganism. In some embodiments, even when the microorganism 145 is an aerobic microorganism, the membrane 115 is impermeable to oxygen and oxygen radicals; oxygen radicals may kill the microorganism. Hydrogen peroxide may also be formed in the photoanode chamber 105, and the membrane 115 would keep the hydrogen peroxide from potentially harming the microorganisms 145 in the photocathode chamber 110.

In some embodiments, the membrane 115 is permeable to anions. Examples of anion permeable membranes include Selemion-DW (AGC Engineering Co., Ltd., Chiba, Japan) and AMI-7001 (Membranes International, Inc., Ringwood, N.J.). When the water used in the artificial photosynthesis system is at neutral pH, a membrane permeable to anions can be used. To maintain charge neutrality during reactions when the system is operating, protons need to be transported between the photoanode assembly 127 and the photocathode assembly 137. There are two methods by which this can be accomplished. One is transporting the protons themselves (e.g., using a membrane permeable to protons). Another is transporting a buffer anion (e.g., such as phosphate or bicarbonate). For example, if a $HCO_3^-$ anion passes through the membrane 115 (e.g., an anion exchange membrane), it can release a proton by forming a carbonate ion ($CO_3^{2-}$). Both methods can balance the proton gradient. When a membrane permeable to anions is used, a buffer salt (e.g., such as phosphate or bicarbonate) is dissolved in the water.

When the system 100 is in operation, the photoanode chamber 105 and the photocathode chamber 110 are filled with water, with the water contacting the photoanode assembly 127, the photocathode assembly 137, the membrane 115, and the microorganism 145. In order for the system 100 to operate, the water needs to be conductive. In some embodiments, a salt is dissolved in the water to make the water conductive. In some embodiments, the salt is an inorganic salt. In some embodiments, the water is a brackish water. Brackish water is water that has more salinity than fresh water, but not as much as seawater. In some embodiments, about 0.5 grams/liter (g/L) to 30 g/L of salt is dissolved in the water. In some embodiments, the salt comprises sodium chloride, sodium phosphate, sodium sulfate, calcium chloride, magnesium chloride, ammonium chloride, or magnesium sulfate.

In some embodiments, the photocathode chamber 110 includes an inlet 150. In some embodiments, the photocathode chamber 110 includes an outlet 155. The inlet 150 is operable to allow carbon dioxide or a gas mixture including carbon dioxide to flow though the water and be dissolved in the water. In some embodiments, the gas mixture includes carbon dioxide and an inert carrier gas (e.g., nitrogen). The outlet 155 is operable to allow a portion of the carbon dioxide not dissolved in the water and/or the inert carrier gas to flow out of the photocathode chamber 110. In some embodiments, the membrane 115 is tilted at an angle of about 1° to 10° with respect to the horizontal (i.e., a truly horizontal or level surface). The membrane 115 shown in FIG. 1B is tilted with respect to the horizontal. This may allow the carbon dioxide not dissolved in the water to flow out of the photocathode chamber 110 through the outlet 155 instead of collecting on the underside of the membrane 115.

As shown in FIG. 1C, in some embodiments, when the system 100 is in operation, a first light 170 irradiates the photoanode assembly 127 and a second light 175 irradiates the photocathode assembly 137. For example, when sunlight (e.g., the first light) irradiates the photoanode assembly 127, some wavelengths of the sunlight may be absorbed and/or blocked by the photoanode assembly 127. The membrane 115 may also absorb and/or block some wavelengths of the sunlight. Then, sunlight without the wavelengths absorbed and/or blocked by the photoanode assembly 127 and/or the membrane 115 (e.g., the second light 175) irradiates the photocathode assembly 137.

In some embodiments, the photoanode assembly 127 comprises an n-type semiconductor having a larger band gap than the p-type semiconductor of the photocathode assembly 137. The band gap is an energy range in the semiconductor where no electron states exist. When the system 100 is in operation, electrons (i.e., the majority carriers) in the photoanode assembly 127 are promoted to the conduction band of the n-type semiconductor of the photoanode assembly 127 by the first light. Holes (i.e., the majority carrier) in the photocathode assembly 137 are promoted to the conduction band of the p-type semiconductor of the photocathode assembly 137 by the first light. The majority carriers (i.e., electrons) of the n-type semiconductor of the photoanode assembly 127 and the majority carriers (i.e., holes) of the p-type semiconductor of the photocathode assembly 137 are transported out of their respective photoactive materials (i.e., the photoanode assembly 127 and the photocathode assembly 137) along the electrical connection 140 as electric current. Because the electrons are negatively charged and the holes are positively charged, the electrons and holes are travelling in opposite directions in the electrical connection 140 and recombine at some point in the electrical connection 140 to complete the electric circuit. The minority carriers (i.e., holes) of the n-type semiconductor of the photoanode assembly 127 and the minority carriers (i.e., electrons) of the p-type semiconductor of the photocathode assembly 137 participate in chemical reactions.

In some embodiments, the photoanode assembly 127 oxidizes water and the photocathode assembly 137 provides an electron that the microorganism 145 uses as a reducing equivalent. In some embodiments, the photoanode assembly 127 oxidizes water and the photocathode assembly 137 generates hydrogen gas ($H_2$) that the microorganism 145 uses as a reducing equivalent. The term reducing equivalent refers to any number of chemical species which transfer the equivalent of one electron in biochemical redox reactions.

In some embodiments, the system 100 includes a filter 160 (not shown in FIG. 1C). In some embodiments, the filter 160 blocks wavelengths of light that are harmful to the microorganism 145. In some embodiments, the filter comprises an ultraviolet light (UV) filter and is positioned to block UV light from the light that irradiates the photocathode assembly 137. UV light is light having a wavelength of about 400 nm to 10 nm, and is harmful to some microorganisms.

The microorganism 145 in the photocathode chamber 110 functions as a biocatalyst for reducing carbon dioxide and forming a carbon-based compound. In some embodiments, the microorganism is selected from a group consisting of bacteria and archaea.

For example, in some embodiments, the microorganism comprises a bacteria belonging to the genus *Sporomsa*. In such embodiments, the bacteria reduces carbon dioxide using electrons as a reducing equivalent and generates acetic acid or acetate. In some embodiments, when electrons are the reducing equivalent, the microorganism 145 is disposed on the plurality of nanowires 130 of the photocathode assembly 137.

In some embodiments, the microorganism 145 comprises knallgas bacteria. Knallgas bacteria, also referred to as hydrogen oxidizing bacteria, oxidize hydrogen as a source of energy with oxygen as a final electron acceptor. When the amount of nitrogen dissolved in the water when the system 100 is in operation is low (e.g., less than about 0.1 to 1 gram per liter (g/L) of ammonium cations), some species knallgas bacteria can generate polyhydroxybutyrate (PHB), a bioplastic. Some species of knallgas bacteria can generate ethanol, isopropanol, isobutanol, methionine, fatty acids, or other carbon-based compounds.

In some embodiments, the microorganism 145 comprises an archaea belonging to the genus *Methansarcina*. In such embodiments, the archaea may reduce carbon dioxide using hydrogen as a reducing equivalent and generate methane.

The system 100 shown in FIGS. 1B and 1C has the photoanode assembly 127 disposed over the photocathode assembly 137. This allows for multiple units of the system 100 to be placed in close proximity of one another to increase the usage of sunlight for a given area. Alternatively, a large area photocathode assembly 127 and a large area photoanode assembly 137 could be used, which would also increase the usage of sunlight for a given area. Other configurations of an artificial photosynthesis system are possible, however.

Figure 3:
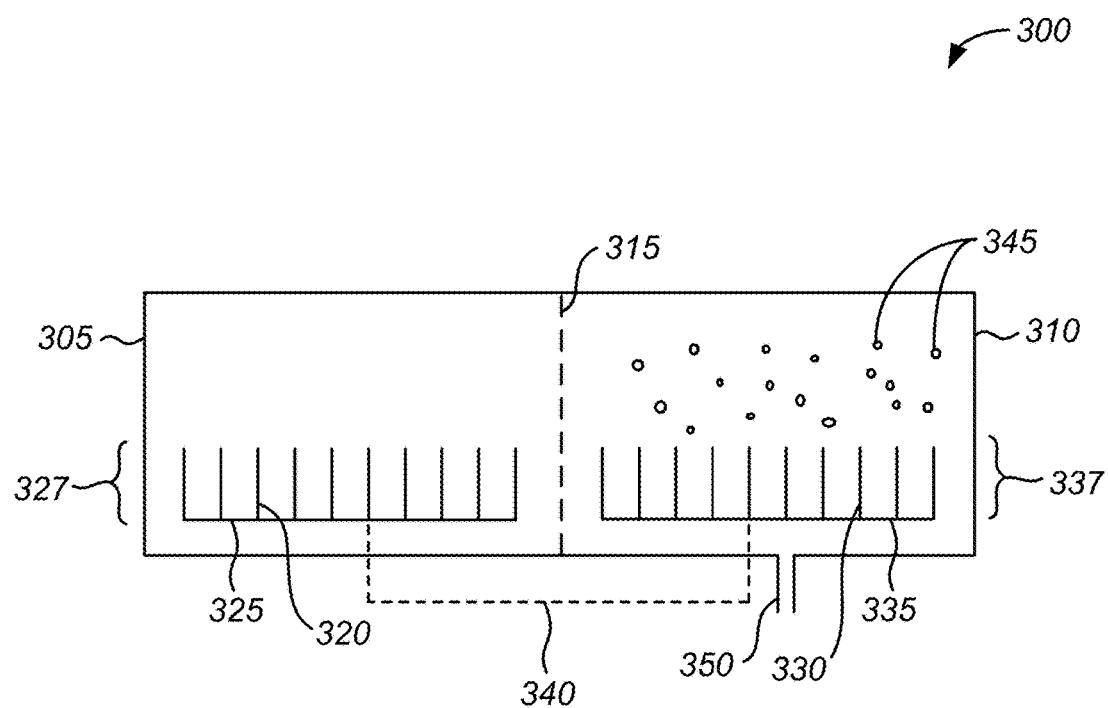
FIG. 3 shows an example of a cross-sectional schematic illustration of an artificial photosynthesis system.

FIG. 3 shows an example of a cross-sectional schematic illustration of an artificial photosynthesis system. As shown, an artificial photosynthesis system 300 includes a photoanode chamber 305, a photocathode chamber 310, and a membrane 315 separating the photoanode chamber 305 and the photocathode chamber 310. The photoanode chamber 305 includes a photoanode assembly 327. In some embodiments, the photoanode assembly 327 comprises a substrate 325. In some embodiments, the photoanode assembly 327 comprises a plurality of nanowires 320 disposed on the substrate 325. Similarly, the photocathode chamber 310 includes a photocathode assembly 337. In some embodiments, the photocathode assembly 337 comprises a substrate 335. In some embodiments, the photocathode assembly 337 comprises a plurality of nanowires 330 disposed on the substrate 335. An electrical connection 340 electrically connects the photoanode assembly 327 and the photocathode assembly 337. A microorganism 345 is disposed in the photocathode chamber 310. The photocathode chamber 310 include an inlet 350 operable to allow carbon dioxide to flow though the water and be dissolved in the water when the system 300 is in operation.

The artificial photosynthesis system 300 has a horizontal layout of the photoanode chamber 305 and the photocathode chamber 310 compared to the vertical stacking of the photoanode chamber 105 and the photocathode chamber 110 of the artificial photosynthesis system 100. In the artificial photosynthesis system 300, light (e.g., sunlight) having the same wavelengths may irradiate the photoanode assembly 327 and the photocathode assembly 337. The artificial photosynthesis system 300 may include filters to control the wavelengths of light irradiating the photoanode assembly 327 and the photocathode assembly 337. Different filters may be used for the photoanode assembly 327 and the photocathode assembly 337.

In a process to fabricate the system 100 shown in FIGS. 1B and 1C and the system 300 shown in FIG. 3, nanowires may be formed using a number of different methods known by one have ordinary skill in the art. For example, nanowires may be formed using chemical vapor deposition (CVD), physical vapor deposition (PVD), laser ablation, hydrothermal processes, and reactive ion etching.

Further, nanostructures other than nanowires may be used in an artificial photosynthesis system. For example, nanoparticles or nanorods disposed on a substrate may be used for the electrodes in an artificial photosynthesis system.

Figure 4:
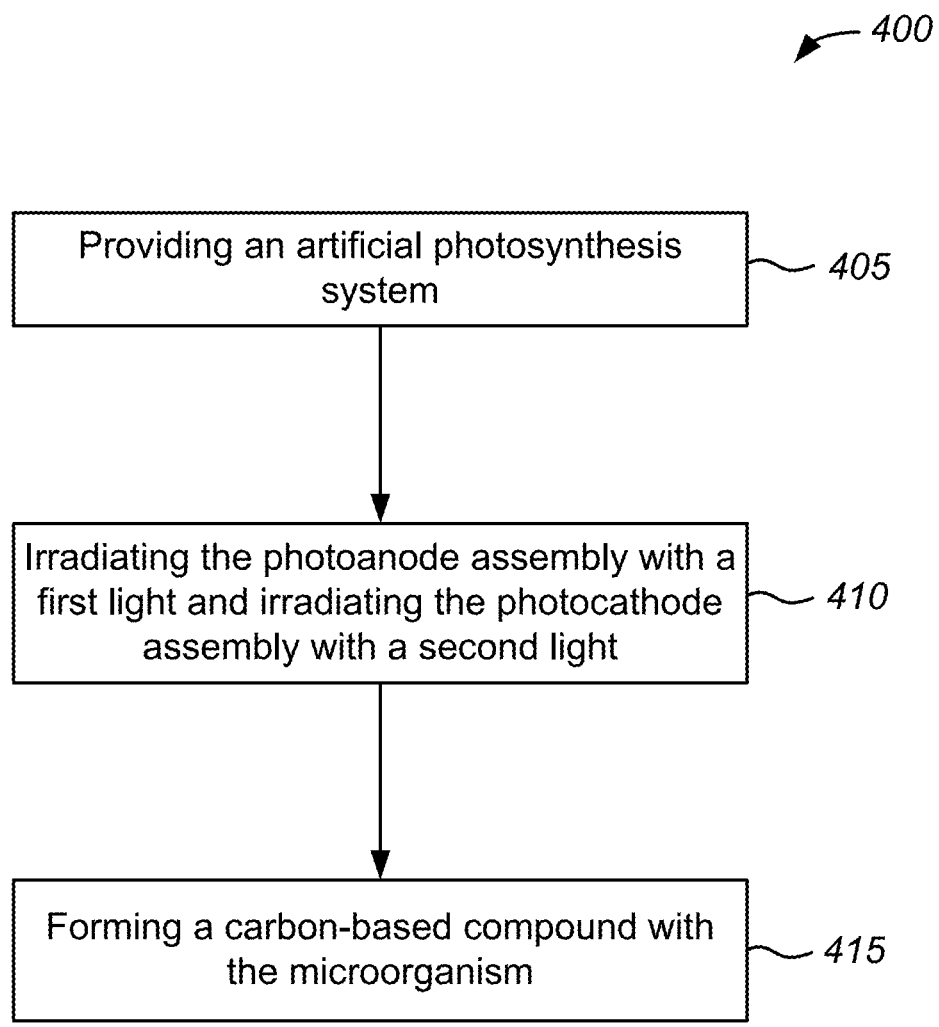
FIG. 4 shows an example of a flow diagram illustrating a method of using an artificial photosynthesis system.

FIG. 4 shows an example of a flow diagram illustrating a method of using an artificial photosynthesis system. At block 405 of the method 400, an artificial photosynthesis system is provided. The artificial photosynthesis system may be any of the artificial photosynthesis systems described herein, including the system 100 shown in FIGS. 1B and 1C and the system 300 shown in FIG. 3. Further, details of the operation of the artificial photosynthesis systems 100 and 300 described in FIGS. 1B and 1C and FIG. 3, respectively, are applicable to the method 400 described in FIG. 4.

At block 410 of the method 400, the photoanode assembly is irradiated with a first light and the photocathode assembly is irradiated with a second light. In some embodiments, the first light includes more wavelengths of light than the second light. In some embodiments, the first light comprises sunlight, and the second light comprises sunlight with some wavelengths of the sunlight removed. In some embodiments, the first light and the second light are the same light and include the same wavelengths of light. In some embodiments, the first light and the second light comprise sunlight.

The photoanode assembly oxidizes water to generate oxygen, protons, and electrons. In some embodiments, the water has about 0.5 grams/liter to 30 grams/liter of salt dissolved in the water. The electrons are provided to the photocathode assembly by the electrical connection. The protons travel through the membrane to the photocathode chamber.

At block 415 of the method 400, the microorganism reduces carbon dioxide and generates a carbon-based compound using the electrons or hydrogen formed by two protons.

In a first example implementation, the plurality of nanowires of the photoanode assembly comprised titanium oxide, the plurality of nanowires of the photocathode assembly comprised silicon, and the microorganism comprised *Sporomsa ovata*. The carbon-based compound that *Sporomsa ovata* generated comprised acetate. In this example implementation, nanowires of the plurality of silicon nanowires were coated with a 30 nm layer of $TiO_2$ to passivate the silicon nanowires.

*Sporomsa ovata* is an anaerobic homoacetogen that metabolizes $CO_2$ via the energy-efficient Wood-Ljungdahl pathway. The titanium oxide nanowires and the silicon nanowires both absorb light and provide a thermodynamic driving force for $CO_2$ reduction. The *Sporomsa ovata* reduced $CO_2$ under mild conditions (e.g., aerobic atmosphere, neutral pH, and temperatures under 30° C.) and produced acetate for up to 200 h under simulated sunlight, with an energy-conversion efficiency of up to 0.38%.

In this example implementation, using a configuration of an artificial photosynthesis system similar to the artificial photosynthesis system 100 shown in FIGS. 1B and 1C, a local anaerobic environment was created in the volume where the nanowires contacted the substrate of the photocathode assembly. The anaerobic environment may be created by depleting oxygen in this volume by oxygen reduction in the aqueous electrolyte, $4H^+ + O_2 + 4e^- \rightarrow 2H_2O$. Further, the nanowires of the photocathode assembly may slow the diffusion of oxygen, which may also aid in creating an anaerobic environment.

In this example implementation, titanium oxide ($TiO_2$) nanowire photoanodes were synthesized via hydrothermal methods. After growth, the nanowire electrode was annealed in air for 30 min at 450° C., and then coated with 10 nm titanium via atomic layer deposition (ALD) to enhance the photoresponse. The resultant titanium oxide nanowire photoanode absorbed UV light of the solar spectrum and was capable of oxidizing water at neutral pH conditions.

Silicon nanowire arrays were fabricated using reactive-ion etching of patterned single-crystalline silicon wafers. To enhance the performance of the silicon nanowire photocathodes, a thin highly doped $n^+$ layer was formed on the surface of the lightly doped p-Si nanowires for better photovoltage output. Additionally, a 30 nm conformal-coated $TiO_2$ layer was deposited at 300° C. via ALD in order to maintain stable performance in a pH neutral electrolyte for prolonged periods of time. Moreover, about 10 nm of nickel was quasi-conformal sputtered onto the electrode, to enhance the charge transfer from the electrode to the bacteria.

In a second example implementation, the plurality of nanowires of the photoanode assembly comprised titanium oxide, the substrate of the photocathode assembly comprised indium phosphide, and the microorganism comprised *Methansarcina barkeri*. The carbon-based compound that the *Methansarcina barkeri* generated comprised methane.

*Methanosarcina barkeri* is an autotrophic obligately anaerobic archaeon that fuels its metabolism via the 8-proton, 8-electron reduction of $CO_2$ to $CH_4$. *M. barkeri* is amenable to integration with inorganic catalysts for a variety of reasons. *M. barkeri* can use $H_2$ as a source of reducing equivalents for the reduction of $CO_2$ to $CH_4$; the photocathode of a water-splitting device can serve as a source of this $H_2$. Owing to the anaerobic metabolism of the organism, oxygen is not required at the cathode, thereby improving Faradaic efficiency for the product of interest, simplifying gas delivery to the culture, and preventing generation of potentially harmful reactive oxygen species. Further, $CH_4$ is generated with high efficiency as a byproduct of normal metabolism. Finally, *M. barkeri* requires no added sources of reduced carbon and can produce $CH_4$ in media which may contain supplemental vitamins and minerals.

In this example implementation, lower than expected Faradaic efficiencies for methane were observed in the experiments; this is in agreement with literature concerning the photosensitivity of methanogenic archaea to blue light. Installation of a 455 nm filter above the photocathode assembly restored the Faradaic efficiency for methane to expected levels.

In this example implementation, the titanium dioxide ($TiO_2$) nanowires of the photoanode assembly were synthesized via a hydrothermal method. A 3×4 cm$^2$ piece of FTO coated glass was cleaned by sonicating in acetone and then three times in isopropanol, and was then blown dry. The freshly cleaned FTO plates were placed in a Teflon-lined autoclave container, conductive side facing down. In a typical synthesis, 0.5 mL titanium tetraisopropoxide was injected into 30 mL of 6 M HCl and shaken well before pouring into the Teflon container such that 75% of the FTO substrate was immersed. The assembled autoclave was placed into a preheated oven at 200° C. for 2 h to 2.5 h. To terminate growth, the autoclave was removed from the oven and cooled to room temperature for 3 h before opening.

The coated FTO plates were removed and rinsed with $dH_2O$, and then blown dry before being annealed in air (30 minute ramp to 450° C., 30 minute anneal, followed by natural cooling). They were subsequently placed in the chamber of an ALD system and coated with 10 nm of amorphous $TiO_2$ (precursors were $TiCl_4$ and $H_2O$).

To assemble the electrode, a 0.5×2 cm$^2$ piece of conductive double-sided carbon tape was placed in the region at the top of the anode that was not coated with n-$TiO_2$ nanowires (and hence remained conductive: average resistance should be less than 100Ω). Subsequently, a thin layer of silver paste was applied to the conductive carbon and gently pressed onto a 2×4 cm$^2$ cm piece of Ti foil. Once dry, epoxy was applied around the junction with the Ti foil, taking care to leave no gaps where water could enter the device. The electrode was allowed to dry at ambient temperature in air for at least 24 h before use. The photoactive geometric surface area of the finished cathodes was 9.0 cm$^2$.

To fabricate the indium phosphide (InP) substrate of the photocathode assembly, a 5 nm layer of Zn and a 50 nm layer of Au were sequentially thermally evaporated onto the back side of an InP wafer. The InP wafer was then subjected to a rapid thermal anneal process (450° C. for 30 min) to fabricate an ohmic contact. The annealing process transforms the Zn—Au layer into a Zn—Au alloy and a fraction of the Zn diffuses into the underlying InP layer, forming a p$^+$-InP layer. The presence of the Zn—Au alloy layer prevents oxidation of metallic Zn. During this step, the color of the film changes from golden yellow to silver. Next, the wafer was sonicated sequentially in acetone and isopropanol and blown dry with $N_2$. The wafer was etched in a 1:1 mixture of concentrated HCl:concentrated $H_3PO_4$ for 5 s to 10 s, then rinsed with $dH_2O$ water three times and blown dry. Immediately after this step, the sample was placed in an ALD chamber and coated with 7 nm to 10 nm of amorphous $TiO_2$ at 150° C. ($TiCl_4$ and $H_2O$ were used as precursors). The $TiO_2$-passivated wafer was sputtered with a 5-nm layer of Pt to act as a HER catalyst.

An approximately 1.5×2 cm$^2$ piece of p-InP/Pt wafer was used to fabricate each electrode. A 1×1 cm$^2$ piece of conductive double-sided carbon tape was placed on the short edge of a 2×6 cm$^2$ piece of titanium foil. Subsequently, a thin layer of silver paste was applied to the back side of the indium phosphide and gently pressed onto the carbon sticker and Ti foil. Once dry, epoxy resin was applied to the front and back of the InP/titanium assembly, taking care to leave no gaps where water could enter the device. The electrode was allowed to dry at ambient temperature in air for at least 24 h before use. The photoactive geometric surface area of the finished cathodes was 3.0 cm$^2$. Before use in experiments, the fabricated electrode was soaked in a media for 24 h to remove any soluble fabrication materials that might be toxic to the cells.

Figure 5:
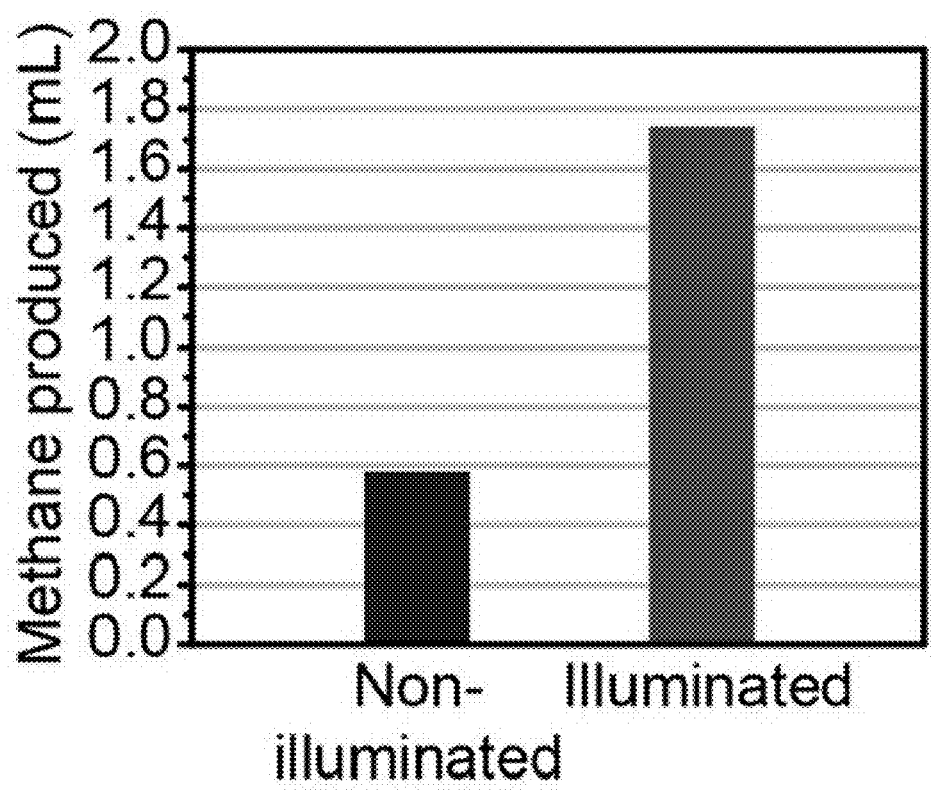
FIG. 5 shows an example of a chart illustrating the average methane produced after 3 days under illuminated (2 independent experiments) and unilluminated (3 independent experiments) conditions using an n-$TiO_2$ photoanode and a p-InP/Pt photocathode with no applied potential.

FIG. 5 shows an example of a chart illustrating the average methane produced after 3 days under illuminated (2 independent experiments) and unilluminated (3 independent experiments) conditions using an n-$TiO_2$ photoanode and a p-InP/Pt photocathode with no applied potential.

CONCLUSION

Further information regarding the artificial photosynthesis systems and methods described herein can be found in Liu et al., "Nanowire-bacteria hybrids for unassisted solar carbon dioxide fixation to value-added chemicals," Nano Lett., 2015, 15 (5), pp 3634-3639 and Nichols et al., "Hybrid bioinorganic approach to solar-to-chemical conversion," PNAS, Sep. 15, 2015, vol. 112, no. 37, 11461-11466, both of which are herein incorporated by reference.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A system comprising:
    a photoanode chamber including a photoanode assembly, the photoanode assembly comprising a first plurality of nanowires disposed on a first substrate;
    a photocathode chamber including a photocathode assembly, the photocathode assembly comprising a second plurality of nanowires disposed on a second substrate;
    an ultraviolet light (UV) filter positioned to block UV light from irradiating the photocathode assembly;
    an electrical connection electrically connecting the photoanode assembly and the photocathode assembly;
    a membrane separating the photoanode chamber and the photocathode chamber, the photoanode assembly operable to oxidize water to generate oxygen, protons, and electrons, the membrane being permeable to the protons and operable to allow the protons to travel to the photocathode chamber, the electrical connection operable to provide electrons to the photocathode assembly; and
    a microorganism disposed in the photocathode chamber, the microorganism comprising a metabolic pathway to reduce carbon dioxide and to generate a carbon-based compound using the electrons or hydrogen formed by two protons, the microorganism comprising an archaea belonging to the genus *Methansarcina*.

2. The system of claim 1, wherein the first plurality of nanowires comprises titanium oxide, wherein the second plurality of nanowires comprises indium phosphide, wherein the microorganism comprises *Methansarcina barkeri*, and wherein the carbon-based compound comprises methane.

3. The system of claim 1, wherein the microorganism is disposed on the second plurality of nanowires of the photocathode assembly.

4. The system of claim 1, wherein the photoanode assembly, the photocathode assembly, the membrane, and the microorganism are disposed in water when the system is in operation, and wherein the water has about 0.5 grams/liter to 30 grams/liter of a salt dissolved in the water.

5. The system of claim 4, wherein the photocathode chamber includes an inlet and an outlet, wherein the inlet is operable to allow the carbon dioxide to flow though the water and be dissolved in the water, and wherein the outlet is operable to allow a portion of the carbon dioxide not dissolved in the water to flow out of the photocathode chamber.

6. The system of claim 1, wherein the first plurality of nanowires is disposed on the first substrate with an end of each of the first plurality of nanowires being in contact with the first substrate, and wherein a length of each of the first plurality of nanowires forms an angle with the substrate of about 45 degrees to 90 degrees.

7. The system of claim 1, wherein the membrane is impermeable to oxygen and oxygen radicals.

8. The system of claim 1, wherein the photocathode assembly is coated with an oxide layer.

9. The system of claim 1, wherein the photocathode assembly is coated with a metal layer.

10. The system of claim 1, wherein the photoanode assembly comprises an n-type semiconductor, and wherein the photocathode assembly comprises a p-type semiconductor.

11. The system of claim 10, wherein the n-type semiconductor has a larger band gap than the p-type semiconductor.

12. A method comprising:
    providing a device comprising:
        a photoanode chamber including a photoanode assembly, the photoanode assembly comprising a first plurality of nanowires disposed on a first substrate;
        a photocathode chamber including a photocathode assembly, the photocathode assembly comprising a second plurality of nanowires disposed on a second substrate;
        an ultraviolet light (UV) filter positioned to block UV light from irradiating the photocathode assembly;
        an electrical connection electrically connecting the photoanode assembly and the photocathode assembly;
        a membrane separating the photoanode chamber and the photocathode chamber, the photoanode, the photocathode, and the membrane being disposed in water, and the membrane being impermeable to oxygen and oxygen radicals; and
        a microorganism disposed in the photocathode chamber, the microorganism comprising an archaea belonging to the genus *Methansarcina;*
    irradiating the photoanode assembly with a first light and irradiating the photocathode assembly with a second light, the photoanode oxidizing the water to generate oxygen, protons, and electrons, the electrons being provided to the photocathode assembly by the electrical connection, the protons travelling through the membrane to the photocathode chamber; and
    forming a carbon-based compound with the microorganism using the electrons or hydrogen formed by two protons.

13. The method of claim 12, wherein the water has about 0.5 grams/liter to 30 grams/liter of salt dissolved in the water.

14. The method of claim 12, wherein the first light includes more wavelengths of light than the second light.

15. The method of claim 12, wherein the photoanode assembly comprises an n-type semiconductor, and wherein the photocathode assembly comprises a p-type semiconductor.

16. The method of claim 12, wherein the first plurality of nanowires comprises titanium oxide, wherein the second substrate plurality of nanowires comprises indium phosphide, wherein the microorganism comprises *Methansarcina barkeri*, and wherein the carbon-based compound comprises methane.

17. The method of claim 12, wherein the microorganism is disposed on the second plurality of nanowires of the photocathode assembly.

18. The method of claim 12, wherein the first plurality of nanowires is disposed on the first substrate with an end of each of the first plurality of nanowires being in contact with the first substrate, and wherein a length of each of the first plurality of nanowires forms an angle with the substrate of about 45 degrees to 90 degrees.

19. The method of claim 12, wherein the photocathode assembly is coated with an oxide layer.

20. The method of claim 12, wherein the photocathode assembly is coated with a metal layer.

\* \* \* \* \*